US007758815B2

(12) United States Patent
Hartselle (10) Patent No.: US 7,758,815 B2
(45) Date of Patent: Jul. 20, 2010

(54) SPECIMEN COLLECTION, STORAGE, TRANSPORTATION AND ASSAYING DEVICE

(76) Inventor: R. Lawrence Hartselle, 1312 Toney Dr., Huntsville, AL (US) 35802

( * ) Notice: Subject to any disclaimer, the term of this patent is extended or adjusted under 35 U.S.C. 154(b) by 1331 days.

(21) Appl. No.: 10/910,180

(22) Filed: Aug. 3, 2004

(65) Prior Publication Data

US 2006/0029517 A1 Feb. 9, 2006

(51) Int. Cl.
G01N 21/01 (2006.01)
G01N 31/22 (2006.01)
G01N 33/48 (2006.01)
G01N 33/52 (2006.01)

(52) U.S. Cl. ............................ 422/102; 422/58; 422/61; 422/68.1; 422/101

(58) Field of Classification Search ................. 422/58, 422/61, 68.1, 101, 102; 436/165
See application file for complete search history.

(56) References Cited

U.S. PATENT DOCUMENTS

| 4,805,632 | A |   | 2/1989  | Pope            |         |
|-----------|---|---|---------|-----------------|---------|
| 4,852,560 | A | * | 8/1989  | Hermann et al.  | 600/575 |
| 5,785,044 | A |   | 7/1998  | Meador et al.   |         |
| 5,897,840 | A | * | 4/1999  | Owens et al.    | 422/102 |
| 6,277,646 | B1|   | 8/2001  | Guirguis et al. |         |
| 6,406,922 | B2|   | 6/2002  | Casterlin et al.|         |
| 6,497,843 | B2|   | 12/2002 | Tydings         |         |
| 6,651,487 | B1| * | 11/2003 | Petty           | 73/61.46|
| 6,669,908 | B2| * | 12/2003 | Weyker et al.   | 422/58  |
| 6,680,027 | B2| * | 1/2004  | Kang et al.     | 422/58  |
| 7,300,633 | B2| * | 11/2007 | Hudak et al.    | 422/103 |
| 7,364,699 | B2| * | 4/2008  | Charlton        | 422/66  |
| 2001/0003918 | A1| * | 6/2001 | Campbell     | 73/61.54|
| 2002/0009390 | A1| * | 1/2002 | Lappe et al. | 422/58  |
| 2003/0021727 | A1|   | 1/2003 | Weyker et al.|         |
| 2005/0048670 | A1| * | 3/2005 | Wu et al.    | 436/180 |

* cited by examiner

Primary Examiner—Jill Warden
Assistant Examiner—Paul S Hyun
(74) Attorney, Agent, or Firm—C. Brandon Browning; Maynard Cooper & Gale, PC (57) ABSTRACT

A tamper-proof, point-of-collection specimen assay apparatus including three selectively connectable and sealable chambers, including a first chamber for receiving a specimen, a second chamber housing a specimen testing device and a specimen transfer site positioned between the first chamber and the second chamber for selectively depositing a portion of the specimen from the first chamber into the second chamber and a third chamber having inlets for depositing another portion of the specimen from the first chamber into the third chamber.

56 Claims, 6 Drawing Sheets

SPECIMEN COLLECTION, STORAGE, TRANSPORTATION AND ASSAYING DEVICE

FIELD OF THE INVENTION

This invention relates to a specimen receptacle and method of using same. More particularly, this invention relates to specimen receptacle and point-of-collection assaying system for determining the presence of a substance in a specimen.

BACKGROUND OF THE INVENTION

Point-of-collection specimen assaying devices are well known in the art and are generally used to detect within a specimen, such as urine, the existence of a substance such as a drug or its metabolite. Exemplary specimen assaying devices typically include a cup for collecting the specimen and a testing device supported within the cup for detecting the particular substance.

Because test subjects sometimes desire to falsify or tamper with a specimen test, precautions can be taken to minimize the possibility. Thus, specimen tests are often administered in rooms that include no access to warm water, while others only include access to water that is dyed. In addition to these precautions, various point-of-collection specimen assaying devices include features for minimizing tampering with the devices.

OBJECTS AND SUMMARY OF THE INVENTION

A primary object of the invention is to provide a specimen receptacle and method of using same for collecting, assaying, storing and/or transporting a specimen.

A further primary object of the invention is to provide a specimen receptacle including at least two separate and selectively connectable chambers.

A further primary object of the invention is to provide a specimen receptacle including at least three separate and selectively connectable chambers.

A further primary object of the invention is to provide a specimen receptacle including a means of transferring a predetermined amount of a specimen from one chamber of the receptacle to another chamber of the receptacle.

A further primary object of the invention is to provide a manually activated specimen assaying system.

A further primary object of the invention is to provide a tamper-proof point-of-collection specimen assaying apparatus.

A further primary object of the invention is to provide a specimen receptacle that does not make use of ambient pressure to control the amount of a specimen transferred from a chamber of the receptacle to testing device of the receptacle.

A further primary object of the invention is to provide a specimen receptacle that does not make use of pad pressure to control the amount of a specimen transferred from one chamber of the receptacle to another chamber of the receptacle.

A further object of the invention is to provide a specimen receptacle including a specimen collection chamber and a testing chamber including a specimen testing device wherein the receptacle includes a means of preventing cross-contamination of a specimen within the collection chamber by that portion of the specimen that is tested with the specimen testing device.

Another object of the invention is to provide a specimen receptacle wherein a specimen testing assembly can be inserted into the receptacle after a specimen is deposited into the receptacle.

The various objects of the invention are accomplished by providing a specimen receptacle including a first chamber for receiving a specimen, a second chamber including a specimen testing device and a specimen transfer site positioned between the first chamber and the second chamber, wherein the site connects the first chamber with the second chamber. Alternatively, a specimen receptacle according to the present invention can include a first chamber, a specimen testing device contained within at least a portion of the first chamber and a means of evidencing the presence of moisture within the first chamber prior to the introduction of a specimen into the first chamber. In another embodiment, a specimen receptacle according to the present invention can include a first container defining a first void, a second container nested with the first container and defining a second void, a specimen testing device in fluid communication with the first void and a first passageway connecting the first void with the second void. In yet another embodiment, a specimen receptacle according to the present invention can include a first chamber including a specimen testing device and a floor sloped toward the specimen testing device.

The objects of the invention are further accomplished by providing a method for specimen collection, analysis, transportation and/or storage including providing a specimen receptacle including a first chamber and a second chamber, depositing a specimen into the first chamber and manually causing a first predetermined amount of the specimen within the first chamber to be deposited into the second chamber. Alternatively, a method of collecting, testing, storing and/or transporting a specimen, according to the present invention, can include providing a specimen receptacle including at least two selectively connectable chambers and depositing a specimen in a first one of the at least two chambers.

By "testing device" it is meant a device for analyzing a sample or specimen. Generally, the testing device is used to detect the presence and/or concentration of an analyte in a sample or specimen, or to determine the presence and/or numbers of one or more components of a sample or specimen, or to make a qualitative assessment of a sample or specimen. Analytes can include a compound or composition to be measured that is capable of binding specifically to a ligand, receptor, or enzyme, usually an antibody or antigen such as a protein or drug, or a metabolite. The precise nature of antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference. Analytes can include antibodies and receptors, including active fragments, fragments thereof or specific binding members thereof. An analyte can include an analyte analogue, which is a derivative of an analyte, such as, for example, an analyte altered by chemical or biological methods, such as by the action of reactive chemicals, such as adulterants or enzymatic activity. Analytes can also include a protein, a nucleic acid molecule, such as a DNA fragment, or an etiological agent, such as an infectious agent or organism or a compound which causes disease.

More particularly, the testing devices of the present invention can include, but are not limited to, cuvettes, slides, lateral flow detection devices such as test strip devices and columns. Lateral flow detection devices can further include, but are not limited to, immunoassays, chemical assays and enzymatic assays commonly known in the art, such as but not limited to, single antibody immunoassays, multiple antibody immunoassays, sandwich immunoassays, competitive immunoassays, non-competitive immunoassays and the like, including assays that utilize horseradish peroxidase, alkaline phosphatase, luciferase, antibody conjugates, antibody fragments, fluorescently tagged antibodies, modified antibodies, labeled antibodies, antibodies labeled with colloidal gold, antibodies labeled with colored latex bead, and the like, which are commonly known in the art. Examples of some testing strips or assay strips that can be incorporated into the present invention can be found in the following US patents: U.S. Pat. No. 4,857,453; U.S. Pat. No. 5,073,484; U.S. Pat. No. 5,119,831; U.S. Pat. No. 5,185,127; U.S. Pat. No. 5,275,785; U.S. Pat. No. 5,416,000; U.S. Pat. No. 5,504,013; U.S. Pat. No. 5,602,040; U.S. Pat. No. 5,622,871; U.S. Pat. No. 5,654,162; U.S. Pat. No. 5,656,503; U.S. Pat. No. 5,686,315; U.S. Pat. No. 5,766,961; U.S. Pat. No. 5,770,460; U.S. Pat. No. 5,916,815; U.S. Pat. No. 5,976,895; U.S. Pat. No. 6,248,598; U.S. Pat. No. 6,140,136; U.S. Pat. No. 6,187,269; U.S. Pat. No. 6,187,598; U.S. Pat. No. 6,228,660; U.S. Pat. No. 6,235,241; U.S. Pat. No. 6,306,642; U.S. Pat. No. 6,352,862; U.S. Pat. No. 6,372,515; U.S. Pat. No. 6,379,620; and U.S. Pat. No. 6,403,383. Further examples of assay strips that can be incorporated into the test device can be found in the following U.S. patent applications: Ser. Nos. 09/579,672; 09/579,673; 09/653,032; 60/233,739; 09/915,494; 10/211,199 and 09/860,408. The one or more test strips of the testing device can be of any shape and dimension, but preferably, include a rectangular test strip. The one or more test strips can be used separately or can be arrayed on or in a common support such as a test card or cartridge. Preferably, multiple test strips of a test device can be arranged such that the sample application regions of the test strips, and not the detection zone, can be contacted with a specimen.

By "specimen" it is any material to be tested for the presence and/or concentration of an analyte in a sample, or to determine the presence and/or numbers of one or more components of a sample, or to make a qualitative assessment of a sample. Preferably, a specimen is a fluid sample, preferably a liquid sample. Examples of liquid samples that may be tested include bodily fluids such as blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid or solid specimens may be used to create liquid solutions, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can include biological materials, such as cells, microbes, organelles and biochemical complexes. Liquid samples can be made from solid, semisolid or highly viscous materials, such as soils, fecal matter, tissues, organs, biological fluids or other samples that are not fluid in nature. For example, these solid or semi-solid samples can be mixed with an appropriate solution, such as a buffer, a diluent or an extraction buffer. The sample can be macerated, frozen and thawed, or otherwise extracted to form a fluid sample. Residual particulates can be removed or reduced using conventional methods, such as filtration or centrifugation. Other features and objects and advantages of the present invention will become apparent from a reading of the following description, as well as a study of the appended drawings.

DETAILED DESCRIPTION OF PRESENTLY PREFERRED EMBODIMENTS

Figure 1:
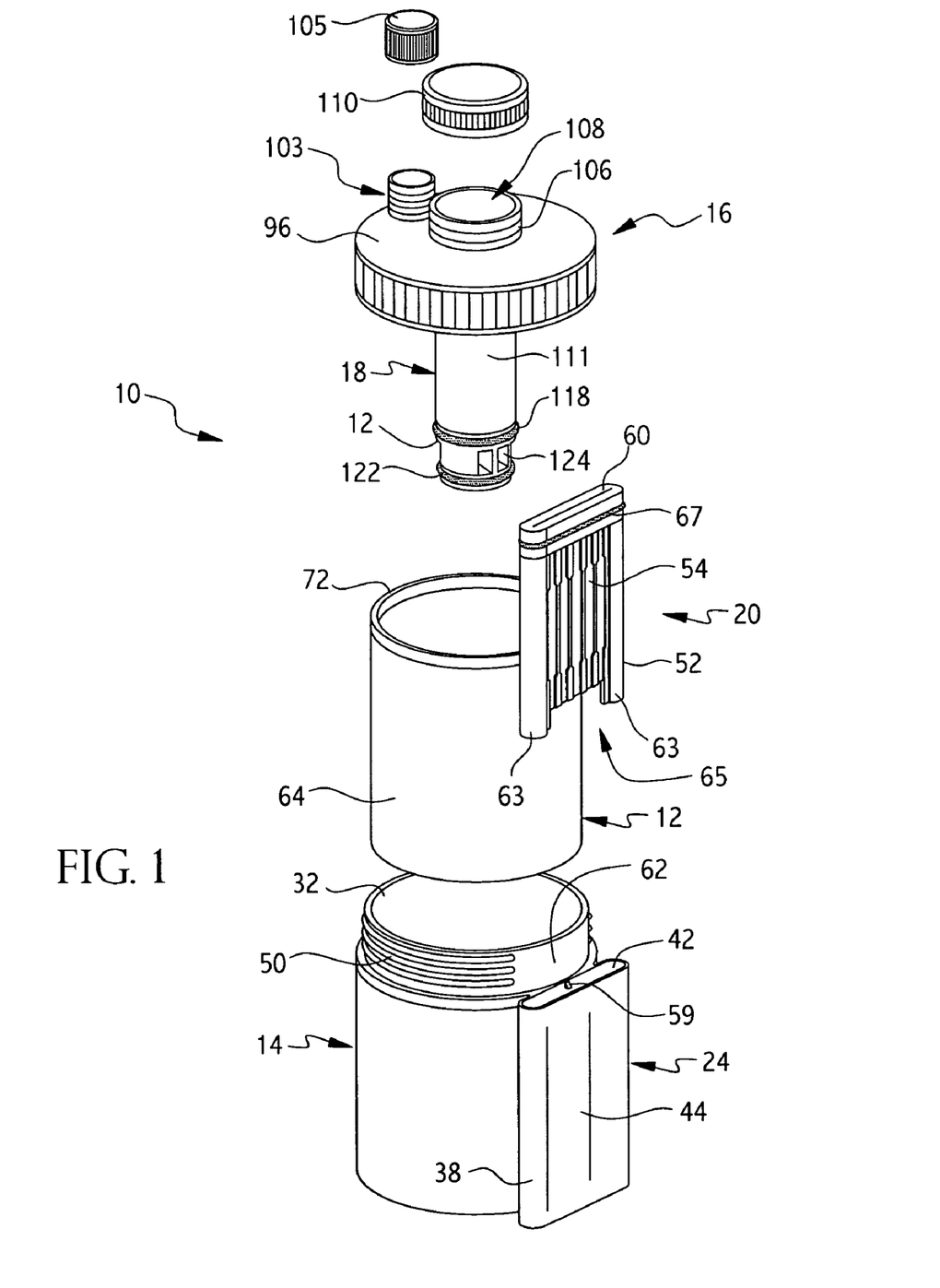
FIG. 1 is an exploded perspective view a specimen receptacle according to the presently preferred embodiment of the present invention.
Figure 2:
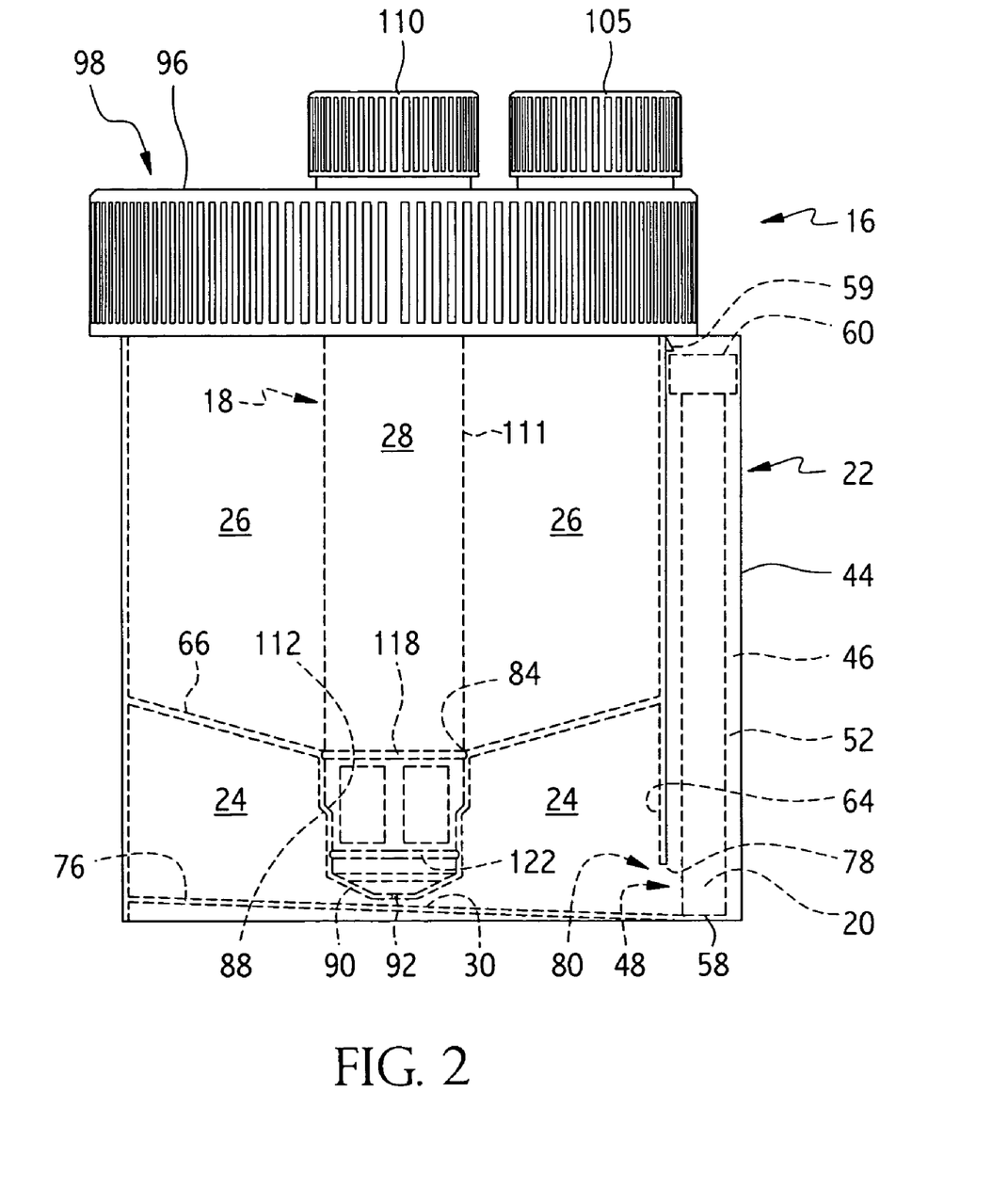
FIG. 2 is a side partial sectional view of the specimen receptacle of FIG. 1.
Figure 3:
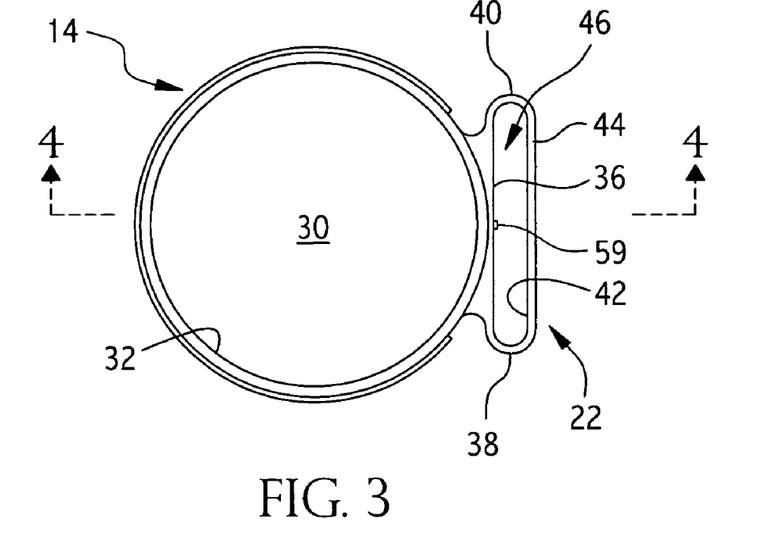
FIG. 3 is a top plan view of an outer container of the specimen receptacle according to FIG. 1.

A specimen receptacle for collecting, assaying, transporting and storing a specimen is illustrated in FIGS. 1 through 12, where like portions of the receptacle share like numbering. The receptacle 10 generally includes an inner container 12, an outer container 14, a lid 16, a plunger 18, a specimen assay assembly 20 and a specimen assay assembly compartment 22. Referring to FIG. 2, when receptacle 10 is fully assembled, inner container 2 is nested within outer container 14, lid 16 is screwed onto outer container 16, plunger 18 extends downward from lid 16 into inner container 12 and assay assembly 20 is supported within compartment 22. This arrangement results in the formation, within receptacle 10, of three separate, distinct and selectively connectable chambers including a test chamber 24 between inner container 12 and outer container 14, a collection chamber 26 between lid 16 and plunger 18, on one hand, and inner container 12, on the other hand, and a storage chamber 28 within plunger 18. In use, after a specimen is deposited into collection chamber 26, lid 16 is screwed onto inner container 12 causing a first predetermined amount of the specimen to be forced by plunger 18 from collection chamber 26 into test chamber 24 where it is sealed away from the specimen in collection chamber 26. Simultaneously therewith, a second predetermined amount of the specimen within collection chamber 26 is transferred into storage chamber 28 where it is sealed away from both collection chamber 26 and test chamber 24. Thus, with lid 16 completely seated onto outer container 14, collection chamber 26, test chamber 24 and storage chamber 28 are sealed from one another so that no further fluid communication between the chambers is possible. This way, the collected specimen is separated into three separate and distinct samples.

More particularly, outer container 14 consists of a generally cup-shaped vessel including a substantially flat, circular sloped floor 30, a circular opening 32 opposite thereto and a continuous sidewall 34 extending therebetween connecting floor 30 with opening 32. Arranged along an outer surface 36 of sidewall 34 is specimen assay assembly compartment 22. Compartment 22 is formed by a pair of elongate, U-shaped, opposing lateral sides 38 and 40, each of which extends outward from outer surface 36 and upward from floor 30 before terminating in an aperture 42, and a substantially flat, transparent face 44 spaced-apart from outer surface 36 and connected to and between lateral sides 38 and 40. Together with outer surface 36, lateral sides 38 and 40 and transparent face 44 form a cavity 46 in which specimen assay assembly 20 is supported. Since transparent face 44 is flat, test results shown on specimen assay assembly 20 are easily read and can be photocopied.

Figure 5:
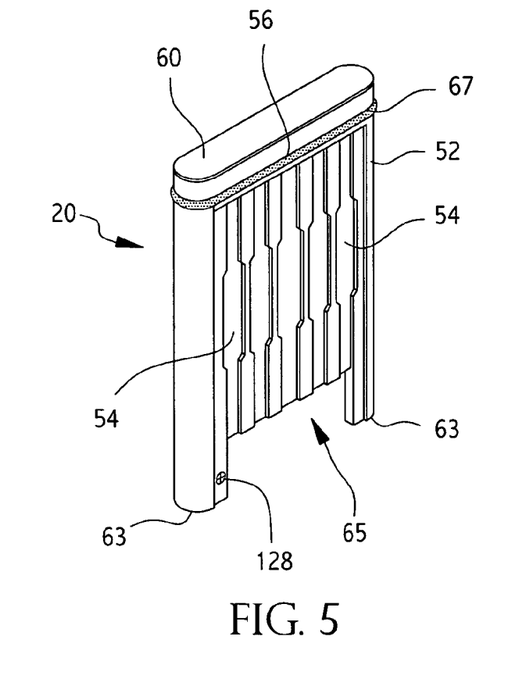
FIG. 5 is a front, perspective view of a specimen assay assembly of the specimen receptacle of FIG. 1.
Figure 6:
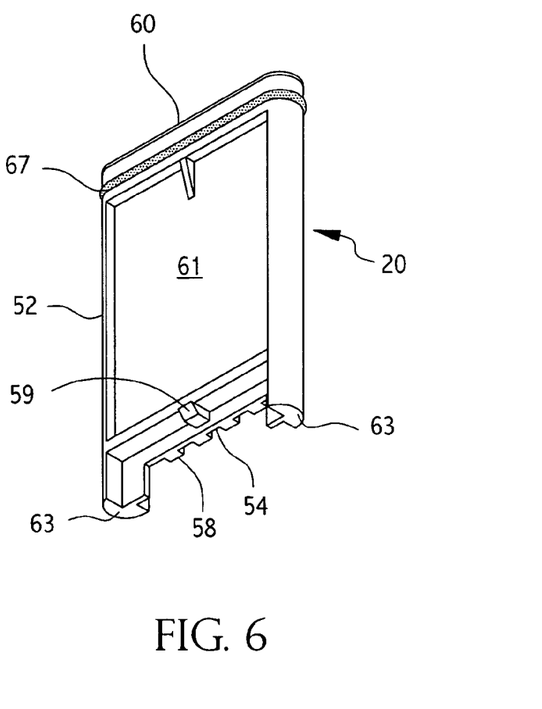
FIG. 6 is a back, perspective view of the specimen assay assembly of FIG. 5.
Figure 7:
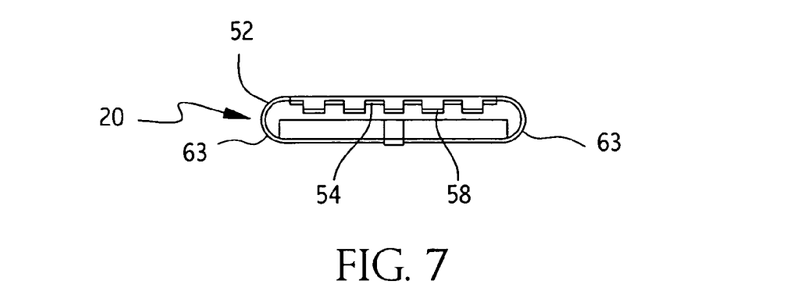
FIG. 7 is an exploded, front view of the specimen assay assembly of FIG. 5.
Figure 8:
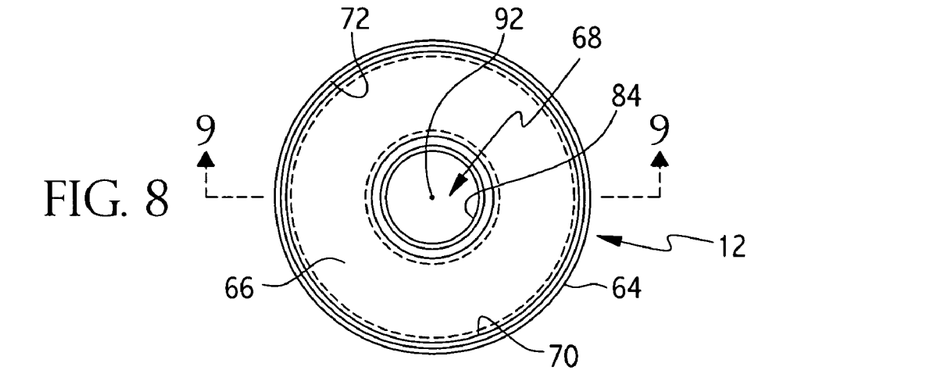
FIG. 8 is a top plan view of an inner container of the specimen receptacle of FIG. 1.

Referring to FIGS. 5 through 7, assay assembly 20 includes a generally rectangular cartridge 52 corresponding to cavity 46 and aperture 42. Cartridge 52 includes a number of vertical, strip receiving slots 54 on a front side 56 thereof positioned substantially parallel to one another for supporting a number of test strips (not shown). As explained above, the test strips of the present invention, can include any number of test strips known in art for detecting any number of substances. Cartridge 52 is inserted into cavity 46 through aperture 42 with front side 56 of cartridge 52 being viewable through transparent face 44. Cartridge 52 is locked within cavity 46 by a protrusion 59 that extends outward from a backside 61 of cartridge 52 and snaps within a slot 48 formed between cavity 46 and test chamber 24. When cartridge 52 is housed within cavity 46, a pair of lateral corners 63 about a bottom side 58 of cartridge rest upon floor 30 forming a gap 65 into which the test strips extend to contact floor 30 within cavity 46. Opposite thereto, cartridge 52 includes a top side 60 that is circumscribed by an O-ring 67 that engages with outer surface 36, lateral sides 38 and 40 and transparent face 44 effectively sealing aperture 42 and cartridge 52 within test chamber 24.

Figure 4:
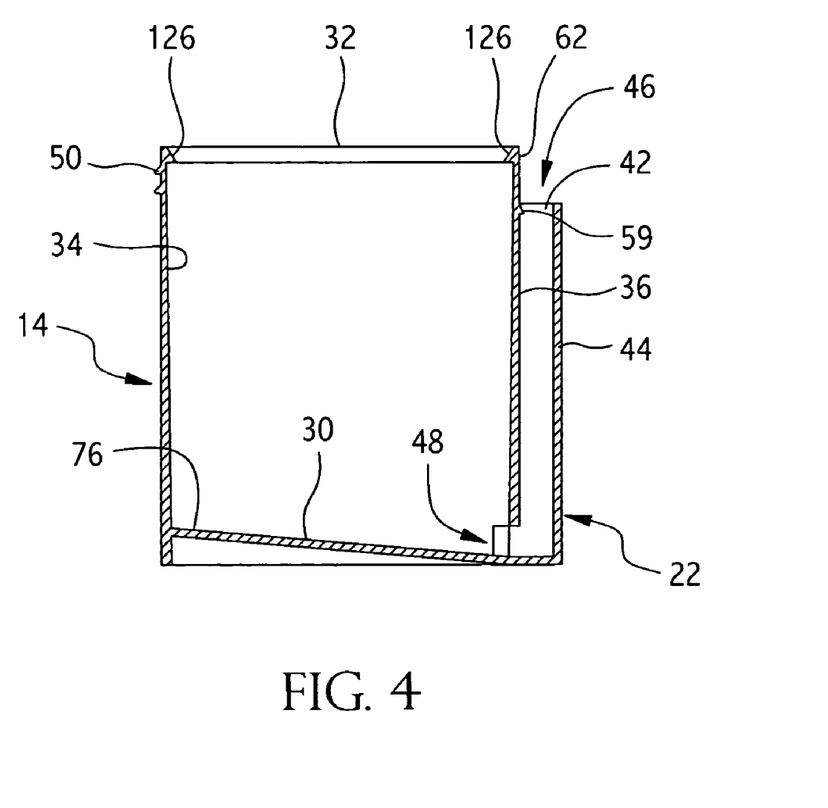
FIG. 4 is a sectional view of the outer container of FIG. 3 along line 4-4.

To fluidly connect cavity 46 of test chamber 24 with test chamber 24, slot 48 is provided within a lower portion of sidewall 34 about its intersection with floor 30. The height, width and shape of slot 48 can vary; however, typically, as illustrated in FIG. 4, slot 48 is generally rectangular-shaped and has a width and a height such that when the first predetermined amount of the specimen is deposited into test chamber 24 and directed toward slot 48, the height of slot 48 is greater than the depth of the specimen at slot 48. This way, the surface tension of the specimen cannot act to preclude or hinder movement of the specimen into cavity 46, a problem associated with other specimen receptacles. To further ensure that any specimen deposited within test chamber 24 is fully directed toward slot 48, cavity 46 and ultimately specimen assay assembly 20, floor 30 is sloped within outer container 14 toward slot 48.

Referring to FIG. 1, a threaded portion 50 partially circumscribes outer surface 36 of outer container 14 immediately below circular opening 32 for connecting lid 16 to outer container 4. Thus, there is an unthreaded portion 62 of outer surface 36 that is situated immediately below circular opening 32 which extends above and between lateral side 38 and 40 of specimen assay assembly compartment 22. Unthreaded portion 62 is provided in order to supply unobstructed access into cavity 46 through aperture 42 so that specimen assay assembly 20 can be inserted into compartment 22.

Figure 9:
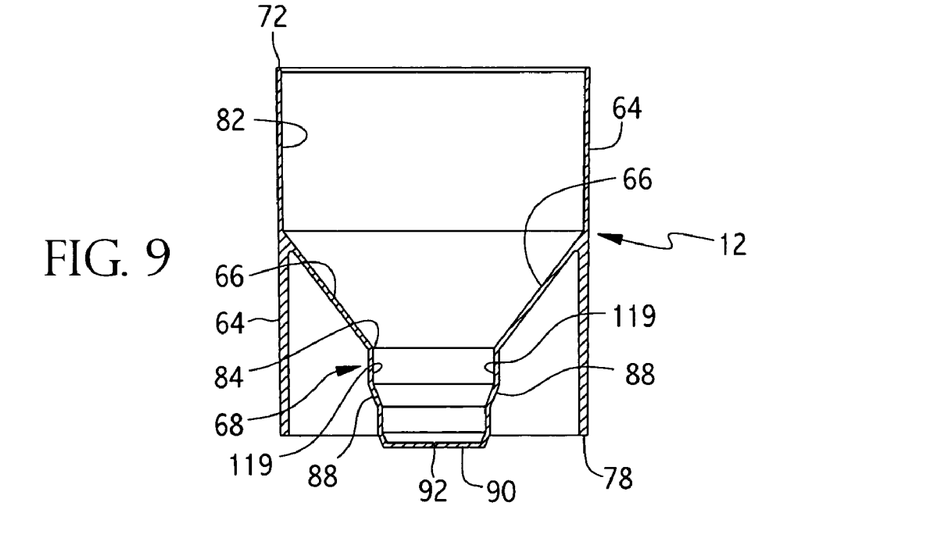
FIG. 9 is a sectional view of the inner container of FIG. 5 along line 6-6.

Nested within outer container 14 is inner container 12. Inner container 12 generally includes a continuous, vertical wall 64, a continuous, conical wall 66 and a plunger receiving portion 68 that forms a centrally located depression within conical wall 66. As illustrated in FIGS. 2 and 9, vertical wall 64 generally runs the vertical length of sidewall 34 of outer container 14, is arranged to lie parallel to and against an inner surface 70 of sidewall 34 and is supported, in part, by a portion of floor 30. Since floor 30 of outer container 14 is sloped, vertical wall 64 only rests upon an upper portion 76 of floor 30, as opposed to that portion of floor 30 about slot 48. As a result of the degree of slope of floor 30, the distance between floor 30 and a lower edge 78 of vertical wall 64 forms a breach 80 having a height and a width large enough to prevent any obstruction of slot 48. Because of this arrangement, inner container 12 can be properly nested within outer container 14, without obstructing slot 48, regardless of the orientation of inner container 12 within outer container 14.

Referring again to FIGS. 2 and 9, conical wall 66 extends inwardly and downwardly from an inside surface 82 of vertical wall 64 before terminating in a centrally located hole 84. Conical wall 66 fulfills at least two functions, one being guiding plunger 18 through collection chamber 26 toward and into hole 84 and another being directing a specimen collected within collection chamber 26 toward and into hole 84. Hole 84 defines a passage into plunger receiving portion 68, which generally forms a cup-shaped chamber shaped to correspond to an end 86 of plunger 18. Thus, plunger receiving portion 68 has a tapered vertical cross-section conforming to the tapered exterior of end 86 of plunger 18 and resulting in a single, inwardly protruding step 88 positioned between hole 84 and a bottom terminus 90 of plunger receiving portion 68.

Figure 9A:
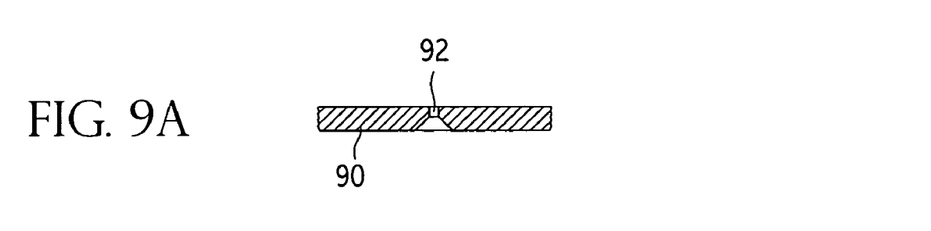
FIG. 9*a* is an enlarged fragmentary view of a specimen transfer site of the inner container of FIG. 9.
Figure 9B:
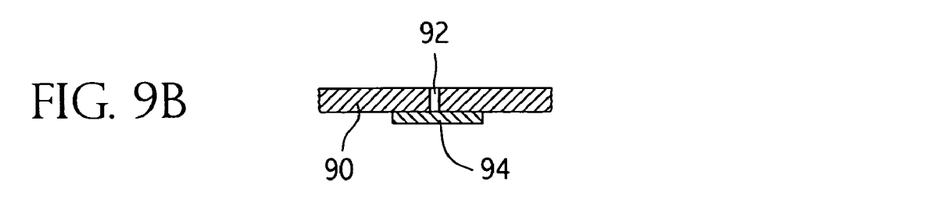
FIG. 9*b* is an enlarged fragmentary view of an alternative arrangement for a specimen transfer site of the inner container of FIG. 9.

As illustrated in FIGS. 9 and 9a, plunger receiving portion 68 further includes an orifice 92 for effecting the selective transfer of a specimen from collection chamber 26 into test chamber 24. To effect the selective transfer of a specimen from collection chamber 26 into test chamber 24, orifice 92 is essentially sealed from collection chamber 26 since its diameter is sufficiently small to prevent the flow of specimen therethrough when the specimen in collection chamber 26 is subject only to ambient pressure. In other words, orifice 92 is sized such that without increasing the pressure exerted on a collected specimen within collection chamber 26, no amount of specimen will pass through orifice 92. As illustrated in FIG. 9b, to further ensure that the transfer of specimen from collection chamber 26 into test chamber 24 cannot occur without additional pressure being exerted onto the collected specimen, orifice 92 can alternatively include a cover member 94 constructed of a thin plastic, paper or foil film and adhered about orifice 92.

To exert the pressure required to selectively transfer an amount of a specimen contained within collection chamber 26 into test chamber 24, lid 16 and plunger 18 are provided. Referring to FIGS. 1, 2 and 10 through 12, lid 16 includes a circular, flat base 96 having an upper side 98, a lower side 100 and a rim 102 extending downwardly from the periphery of base 96. Base 96 further includes a port 103 for providing access through lid 16 and into collection chamber 26 when lid 16 is screwed onto outer container 14. To enclose port 103 a first cap 105 is provided which can be removably connected about port 103.

Centrally located within base 96 of lid 16 and extending perpendicularly therethrough is plunger 18. Plunger 18 extends in one direction through upper side 98 of base 96 and in another direction through lower side 100. That portion of plunger that extends through upper side 98 forms a hollow, threaded neck 106 forming an outlet 108 therein. Outlet 108 provides access into storage chamber 28 and can be removably enclosed by a second cap 110. Opposite threaded neck 106, that portion of plunger 18 that extends through lower side 100 forms a hollow shaft 111 terminating in end 86 and having a length such that when lid 16 is completely screwed onto outer container 14, end 86 is completely seated within plunger receiving portion 68. By seated within plunger receiving portion 68, it is meant that end 86 of shaft 111 includes a tapered arrangement corresponding to and being arranged to engage with the tapered arrangement of plunger receiving portion 68. Thus, end 86 includes a inwardly directed step, corresponding to inwardly protruding step 88 of plunger receiving portion 68, that defines a ridge 112 that encircles end 86 of shaft 111. Ridge 112 and inwardly protruding step 88 are arranged such that when plunger 18 is seated within plunger receiving portion, ridge 112 engages step 88.

Figure 10:
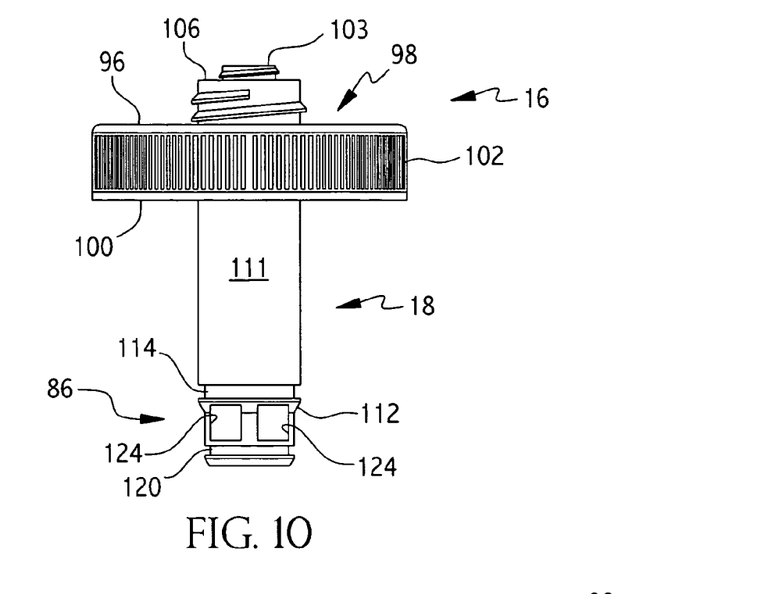
FIG. 10 is an elevational view of a lid and plunger assembly of the specimen receptacle of FIG. 1.
Figure 11:
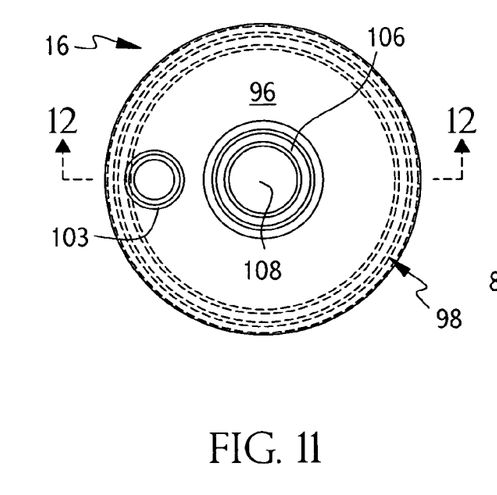
FIG. 11 is a top plan view of the lid and plunger assembly of FIG. 10.
Figure 12:
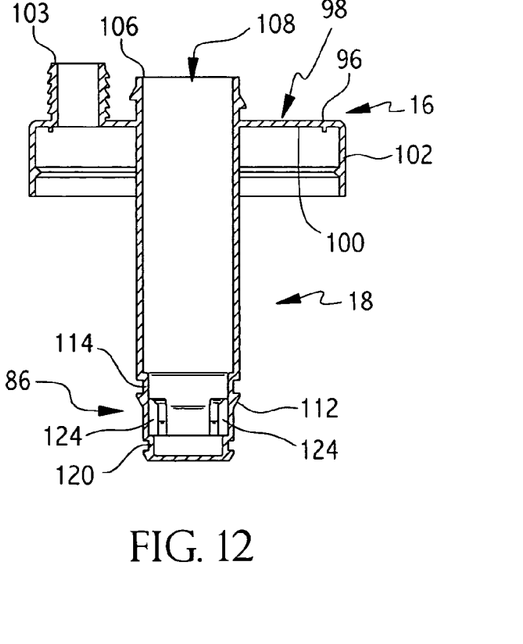
FIG. 12 is a sectional view of the lid and plunger assembly of FIG. 11 along line 12-12.

Positioned on either side of ridge 112 about end 86 of plunger 18 are a pair of respective horizontal, continuous indentations for receiving a pair of respective O-rings which, among other things, act to seal collection chamber 26 from plunger receiving portion 68 and plunger receiving portion 68 from test chamber 24. The indentations are best illustrated in FIGS. 10 and 12, where the O-rings have been removed. Specifically, an upper indentation 114 is arranged about end 86 of plunger 18 such that when end 86 is seated within plunger receiving portion 68, an O-ring 118 within upper indentation 114 is caused to abut a wall 119 of plunger receiving portion 68 immediately below hole 84. Another lower indentation 120 is arranged about end 86 of plunger 18 such that when end 86 of plunger 18 is seated within plunger receiving portion 68, an O-ring 122 within lower indentation 120 is caused to abut another portion of wall 119 of plunger receiving portion 68 below inwardly protruding step 88. This way, the arrangement of O-rings 118 and 122 about end 86 of plunger 18 relative to plunger receiving portion 68 performs several functions, in addition to those discussed above, which will be described hereafter in more detail.

Plunger 118 further includes a pair of rectangular inlets 124 within end 86 thereof for providing fluid access into storage chamber 28. Inlets 124 allow for the selective transfer of about 15 ml of specimen from collection chamber 26 into storage chamber 28, which occurs when end 86 of plunger 18 is inserted through a specimen contained within collection chamber 26. The amount of specimen transferred into storage chamber 28 from collection chamber 26 as end 86 is passed through the specimen is controlled, in part, by the ambient pressure within storage chamber 28, when enclosed by second cap 110, and the sealing of end 86 within plunger receiving portion 68 as described above.

In use, receptacle 10, with lid 16 and plunger 18 removed, is given to a test subject who deposits a specimen, such as urine, into collection chamber 26 of inner container 12. Since collection chamber 26 is effectively sealed, the specimen is collected within collection chamber 26. Because it is well-known that unscrupulous test subjects often attempt to circumvent the test procedure by immersing a testing device of a specimen receptacle in warm water prior to depositing a specimen within the receptacle in order to provide of false negative test result, inner container 12 is locked within outer container 14 by a lip 126 that protrudes outward from inner surface 70 of outer container 14. This way, the test subject cannot deposit water or anything else directly into outer container 14 and cavity 46 in such a way to contact the test strips of specimen assay assembly 22 thereby causing a false negative test result.

After the specimen is collected, the test giver, who is in possession of lid 16 and plunger 18, receives receptacle 10 from the subject and inspects it for evidence of tampering. This typically involves measuring the temperature of the specimen and visually inspecting the integrity of the receptacle. Given receptacle 10 of the present invention, a test giver can now inspect a moisture detector 128 which is provided within cavity 46 and supported by cartridge 52. Detector 128 is located on front side 56 of cartridge 52 so that it can be seen through transparent face 44 and near its intersection with bottom side 58 so that any undesirable liquid deposited within cavity 46 is more likely to contact or otherwise affect detector 128. Detector 128 includes moisture paper which is commonly found in many electronic devices, such as cell phones, for indicating whether the interior of such services have ever been in contact with a liquid. Moisture paper typically includes a visible symbol such as an X on the surface thereof made of a dye. Upon contact with moisture, the X bleeds giving the X a blurred appearance. The bleeding of the dye is proof that moisture of some type has been introduced into test chamber 24 and/or cavity 46 prior to the proper time, i.e., prior to the introduction of the specimen into receptacle 10. This way, a test giver can determine whether the test strips of specimen assay assembly 20 have been tampered with prior to testing.

If receptacle 10 has not been tampered with, the test giver inserts plunger 18, with second cap 110 enclosing passage 104, into collection chamber 26 and through the specimen collected there. As plunger 18 traverses through the collected specimen a predetermined amount of about 15 ml of specimen is allowed to flow into storage chamber 28 through pair of inlets 124. As stated above, this amount is provided for, in part, by the ambient pressure within storage chamber 28. As plunger 18 descends through collection chamber 26, conical walls 66 of inner container 12 help to guide end 86 of plunger 18 toward hole 84 and into plunger receiving portion 68. When O-ring 122 descends below inwardly protruding step 88 of plunger receiving portion 68, O-ring 122 sealingly engages wall 119 of plunger receiving portion 68 aliquotting a predetermined amount of about 1 ml of specimen between O-ring 122 and terminus 90 of plunger receiving portion 68. Thus, as end 86 of plunger 18 descends further into plunger receiving portion 68, the aliquotted amount of specimen is subjected to pressure great enough to force the aliquotted specimen through orifice 92, cover member 94, when present, and into test chamber 24. This continues until ridge 112 of end 86 of plunger 18 is seated upon inwardly protruding step 88 of plunger receiving portion 68. When aliquotted amount of specimen, i.e. about 1 ml, is deposited into test chamber 24 from collection chamber 26, it falls onto floor 30 of outer container 14 which directs the aliquotted specimen into cavity 46. Once in cavity 46, the specimen is allowed to contact the individual test strips supported within test receiving slots 54 where the strips extend into gap 62 between lateral corners 63 of cartridge 52, and the specimen is assayed. The results of the assay can be viewed through transparent face 44, photocopied and recorded.

Often, when an assay produces a positive result indicating that an undesired substance is present in the specimen of the test giver, the test giver will challenge the assay and demand confirmation of the results. For that reason, receptacle 10 is arranged to collect and divide a specimen it into three distinct specimens, each of which can be tested separate and apart from the other specimens. As described above, one such specimen is that specimen deposited into test chamber 24 and tested at the site of collection. Because of the interaction of O-ring 122 with wall 119 of plunger receiving assembly 68, the specimen within test chamber 24 is maintained separate and apart from any specimens contained within the other chambers of receptacle 10 and no contamination by the tested specimen of the other separate specimens can occur.

A second, separate and distinct specimen is that specimen which is transferred into storage chamber 28. This specimen, like the specimen within test chamber 24, is separated from any other specimen within receptacle 10. This is accomplished by the interaction of O-ring 118 with wall 119 of plunger receiving portion 68. Specifically, as illustrated in FIG. 2, when ridge 112 of end 86 of plunger 18 is seated onto inwardly protruding step 88 of plunger receiving portion 68, O-ring 118 is caused to sealingly engage against wall 119 of plunger receiving portion 68 about hole 84. As a result, the specimen transferred from collection chamber 26 into storage chamber 28 as plunger 18 descended through the specimen collected within collection chamber 26 is separated from the remaining specimen within collection chamber 26 by O-ring 118. As described above, the specimen within storage chamber 28 is separated from the specimen contained within test chamber 24 by the interaction O-ring 122 with wall 119 of plunger receiving portion 68. The third, separate and distinct specimen is that specimen remaining within collection chamber 26 after test chamber 24 and storage chamber 28 are sealed, as described above.

With the specimen adequately divided and the test subject demanding confirmation of his test results, receptacle 10 can be transported to an appropriate facility where the specimens contained within storage chamber 28 and collection chamber 26 can be independently tested. Access to the specimen within storage chamber 28 is accomplished by removing second cap 110 from neck 106, while access to the specimen contained within collection chamber 26 is allowed by removing first cap 105 from port 103.

As will be apparent to one skilled in the art, various modifications can be made within the scope of the aforesaid description. Such modifications being within the ability of one skilled in the art form a part of the present invention and are embraced by the claims below.

It is claimed:

1. A specimen receptacle comprising,
   a first chamber arranged for receiving a specimen directly from a test subject,
   a second chamber including a specimen testing device,
   a pressure exerting device disposed at least partially within the first chamber for increasing a pressure within the receptacle, wherein the pressure exerting device defines a third chamber, and
   a specimen transfer site positioned essentially between the first chamber and the second chamber, the specimen transfer site being adapted and arranged for selectively transferring at least a portion of a specimen between the first chamber and the second chamber,
   wherein the specimen testing device does not extend into the third chamber and is not in contact with the pressure exerting device,
   wherein the pressure exerting device is connected with a lid having a top side and a bottom side and the pressure exerting device extends downward from the bottom side of the lid into the first chamber,
   wherein the lid includes an opening in fluid communication with the third chamber defined by the pressure exerting device, and
   wherein the lid further includes a second opening in fluid communication with the first chamber.

2. The specimen receptacle according to claim 1 wherein the first chamber and the second chamber are not in fluid communication.

3. The specimen receptacle according to claim 1 wherein the first chamber and the second chamber are in fluid communication.

4. The specimen receptacle according to claim 1 further comprising a means for transferring a predetermined amount of the specimen within the first chamber directly into the second chamber.

5. The specimen receptacle according to claim 1 wherein the pressure exerting device is vertically arranged within the first chamber.

6. The specimen receptacle according to claim 1 wherein the second chamber includes a testing device support chamber in fluid communication with the second chamber and the specimen testing device is at least partially contained within the specimen testing device support chamber.

7. The specimen receptacle according to claim 6 wherein the second chamber includes a floor sloped toward the testing device support chamber.

8. The specimen receptacle according to claim 1 wherein the second chamber includes a floor sloped toward the specimen testing device.

9. The specimen receptacle according to claim 1 further comprising a cap adapted to cover the opening.

10. The specimen receptacle according to claim 1 further comprising a second cap adapted to cover the second opening.

11. The specimen receptacle according to claim 1 wherein the pressure exerting device is a plunger that is vertically arranged within the receptacle.

12. The specimen receptacle according to claim 11 wherein the first chamber includes a plunger receiving portion for receiving an end of the plunger.

13. The specimen receptacle according to claim 12 wherein the end of the plunger includes a first sealing member for engaging a portion of the plunger receiving portion.

14. The specimen receptacle according to claim 13 wherein the end of the plunger includes a second sealing member for engaging another portion of the plunger receiving portion.

15. The specimen receptacle according to claim 14 wherein the lower wall portion defining the plunger receiving portion includes an opening leading directly between the first chamber and the second chamber.

16. The specimen receptacle according to claim 1 wherein the pressure exerting device includes at least one aperture directly connecting the third chamber with the first chamber.

17. The specimen receptacle according to claim 1 wherein the third chamber includes at least one aperture adapted and arranged for selectively depositing a predetermined amount of a specimen contained within the first chamber into the third chamber.

18. The specimen receptacle according to claim 1 wherein the second chamber further includes a moisture detecting member.

19. The specimen receptacle according to claim 1 wherein the first chamber completely surrounds a portion of the pressure exerting device.

20. A specimen receptacle comprising,
    a first chamber for receiving a specimen,
    a second chamber including a specimen testing device,
    a lid detachably disposed on top of the first chamber, the lid having a top side and a bottom side and a hole extending from the top side to the bottom side, a pressure exerting device integrally formed with the bottom side of the lid, a third chamber defined by the pressure exerting device and being in direct fluid communication with the hole, and a specimen transfer site positioned essentially between the first chamber and the second chamber, the specimen transfer site being adapted and arranged for selectively transferring at least a portion of a specimen directly between the first chamber and the second chamber, wherein the specimen testing device does not extend into the third chamber and is not in contact with the pressure exerting device, wherein the pressure exerting device is connected with the lid and extends downward from a bottom side thereof, wherein the hole in the lid is in fluid communication with the third chamber defined by the pressure exerting device, and wherein the lid further includes a second hole in fluid communication with the first chamber.

21. The specimen receptacle according to claim 20 wherein the first chamber and the second chamber are not in fluid communication.

22. The specimen receptacle according to claim 20 wherein the first chamber and the second chamber are in fluid communication.

23. The specimen receptacle according to claim 20 further comprising a means for transferring a predetermined amount of the specimen within the first chamber directly into the second chamber without passing the specimen through the third chamber.

24. The specimen receptacle according to claim 20 further comprising a closure obstructing the specimen transfer site.

25. The specimen receptacle according to claim 20 wherein the second chamber includes a testing device support chamber in fluid communication with the second chamber and the specimen testing device is completely contained within the specimen testing device support chamber.

26. The specimen receptacle according to claim 25 wherein the second chamber includes a floor sloped toward the testing device support chamber.

27. The specimen receptacle according to claim 20 wherein the lid includes a plunger extending out from the bottom side thereof and into the first chamber.

28. The specimen receptacle according to claim 20 wherein the first chamber includes a plunger receiving portion for receiving an end of a plunger, the receiving portion having an interior surface that directly interacts with the plunger and partially defines the first chamber.

29. The specimen receptacle according to claim 28 wherein the end of the plunger includes at least one sealing member for engaging a portion of the plunger receiving portion.

30. The specimen receptacle according to claim 29 wherein the specimen transfer site is located within the plunger receiving portion.

31. The specimen receptacle according to claim 30 wherein the at least one sealing member is an O-ring.

32. The specimen receptacle according to claim 20 wherein the pressure exerting device is a plunger.

33. The specimen receptacle according to claim 32 wherein the first chamber includes a plunger receiving portion for receiving an end of the plunger.

34. The specimen receptacle according to claim 33 wherein the end of the plunger includes a first sealing member for engaging a portion of the plunger receiving portion.

35. The specimen receptacle according to claim 34 wherein the plunger includes at least one aperture between the first sealing member and a second sealing member.

36. The specimen receptacle according to claim 20 wherein the third chamber includes at least one aperture adapted and arranged for selectively connecting the third chamber with the first chamber.

37. The specimen receptacle according to claim 20 wherein the second chamber further includes a means of detecting moisture.

38. The specimen receptacle according to claim 20 wherein the first chamber completely encircles a length of the pressure exerting device.

39. A specimen receptacle for storing a specimen comprising, a first chamber containing a first portion of the specimen, a detachable lid coupled to a rim of the first chamber, a second chamber including a specimen testing device, the specimen testing device being in contact with a second portion of the specimen, a plunger defining a third chamber, the third chamber containing a third portion of the specimen, an opening through the lid that extends directly into the third chamber, and a specimen transfer site positioned essentially between the first chamber and the second chamber, wherein the second portion is not in fluid communication with the third portion.

40. The specimen receptacle according to claim 39 wherein the second portion is not in fluid communication with the first portion.

41. The specimen receptacle according to claim 39 wherein the specimen testing device does not extend into the third chamber and is not in contact with the plunger.

42. The specimen receptacle according to claim 39 wherein the plunger is connected with the lid.

43. The specimen receptacle according to claim 42 claim wherein the lid further includes a second opening in fluid communication with the first chamber.

44. The specimen receptacle according to claim 39 wherein the first chamber and the second chamber are not in fluid communication.

45. The specimen receptacle according to claim 39 wherein the plunger is vertically arranged within the first chamber.

46. The specimen receptacle according to claim 39 wherein the second chamber includes a testing device support chamber in fluid communication with the second chamber and the specimen testing device is at least partially contained within the specimen testing device support chamber.

47. The specimen receptacle according to claim 46 wherein the second chamber includes a floor sloped toward the testing device support chamber.

48. The specimen receptacle according to claim 39 wherein the second chamber includes a floor sloped toward the specimen testing device.

49. The specimen receptacle according to claim 39 further comprising a cap adapted to cover the opening.

50. The specimen receptacle according to claim 39 wherein the first chamber includes a plunger receiving portion for receiving an end of the plunger.

51. The specimen receptacle according to claim 50 wherein the end of the plunger includes a first sealing member for engaging a portion of the plunger receiving portion.

52. The specimen receptacle according to claim 51 wherein the end of the plunger includes a second sealing member for engaging another portion of the plunger receiving portion.

53. The specimen receptacle according to claim 52 wherein the lower wall portion defining the plunger receiving portion includes an opening leading directly between the first chamber and the second chamber.

54. The specimen receptacle according to claim 39 wherein the plunger includes at least one aperture directly connecting the third chamber with the first chamber.

55. The specimen receptacle according to claim 39 wherein the second chamber includes a moisture detecting member.

56. The specimen receptacle according to claim 39 wherein the first chamber completely surrounds a portion of the pressure exerting device.

* * * * *